United States Patent [19]
Osborn, III

[11] Patent Number: 6,007,528
[45] Date of Patent: Dec. 28, 1999

[54] SANITARY NAPKIN HAVING STABILIZED MEMBERS IN THE END REGIONS

[75] Inventor: Thomas Ward Osborn, III, Cincinnati, Ohio

[73] Assignee: The Procter & Gamble company, Cincinnati, Ohio

[21] Appl. No.: 08/777,661

[22] Filed: Dec. 31, 1996

[51] Int. Cl.⁶ ........................................... A61F 13/15
[52] U.S. Cl. .................... 604/387; 604/385.1; 604/374; 604/368
[58] Field of Search ...................... 604/368, 374, 604/378–380, 385.1, 385.2, 387

[56] References Cited

U.S. PATENT DOCUMENTS

| | | |
|---|---|---|
| 3,570,493 | 3/1971 | Olsson . |
| 3,783,871 | 1/1974 | Sabee .................................. 604/378 |
| 4,405,326 | 9/1983 | Lenaghan . |
| 4,559,051 | 12/1985 | Hanson ................................ 604/378 |
| 5,545,158 | 8/1996 | Jessup ................................ 604/385.2 |
| 5,578,025 | 11/1996 | May . |
| 5,613,961 | 3/1997 | DiPalma et al. ..................... 604/385.2 |
| 5,624,423 | 4/1997 | Anjur et al. ......................... 604/385.1 |
| 5,630,376 | 5/1997 | Ochi et al. .......................... 604/385.2 |

FOREIGN PATENT DOCUMENTS

| | | |
|---|---|---|
| 0 298 348 A1 | 1/1989 | European Pat. Off. . |
| 0 712 619 A2 | 5/1996 | European Pat. Off. . |
| WO 95/31165 | 11/1995 | WIPO . |

Primary Examiner—Mickey Yu
Assistant Examiner—Tram A. Nguyen
Attorney, Agent, or Firm—Theodore P. Cummings; Steven W. Miller; Jacobus C. Rasser

[57] ABSTRACT

The present invention provides an absorbent article preferably being a sanitary napkin that comprises a longitudinal centerline, a transverse centerline, a pair of longitudinal edges, two end edges, a first end region extending from one of the end edges toward the transverse centerline, and a second end region extending from the other end edge toward the transverse centerline. Also, there is a central region positioned between the first and second end regions. The sanitary napkin further comprises a first surface, a second surface that is faced opposite to the first surface wherein the flexure-resistance of the sanitary napkin as measured through the first and second end regions is greater than the flexure-resistance of the sanitary napkin as measured through the central region.

16 Claims, 4 Drawing Sheets

SANITARY NAPKIN HAVING STABILIZED MEMBERS IN THE END REGIONS

FIELD OF THE INVENTION

This invention is a sanitary napkin that comprises end regions and preferably end edges which provide resistance to roll-over at the article ends through the use of stabilizing members therein.

BACKGROUND OF THE INVENTION

This invention is concerned with absorbent articles such as sanitary napkins, pantiliners, and incontinence pads that are designed to absorb and retain liquid and other discharges from the human body and to prevent body and clothing soiling. The present invention is particularly concerned with sanitary napkins that have reduced roll-over at their end regions, particularly their end edges.

Disposable absorbent articles are designed to contain body exudates and to keep such body exudates from soiling adjacent clothing and undergarments. Thus, numerous improvements have been directed towards providing better containment of such body exudates within the sanitary napkin and reducing the occurrence of soiling of garments worn over the sanitary napkin. Soiling of garments resulting from the roll-over of the end edges of sanitary napkins is particularly a problem with catamenials. Soiling at the end edges is caused by a lack of stability in the end regions and/or end edges of a pad. It is therefore desirable to provide a sanitary napkin having a limited range of motion at its ends to prevent soiling caused by roll-over. Additionally, this restricted range of motion will enhance the body-conforming capability of the pad overall.

Additionally, the roll-over of the end of the pad increases the level of discomfort or noticeability of the product by a wearer. Roll-over reduces the effectiveness of the catamenial pad by reducing the effective length of the pad, which may thereby increase the amount of fluid which may directly flow from a wearer to their undergarment.

There have been a number of recent efforts to provide catamenial pads with improved body-conforming characteristics in order to improve the leakage performance of these products. In particular, sanitary napkins have been developed which are relatively thin and flexible to better conform the sanitary napkin to the wearer. Commercially successful sanitary napkins of this type are described in U.S. Pat. No. 4,950,264, issued to Osborn, on Aug. 21, 1990 and U.S. Pat. No. 5,009,653 issued to Osborn, on Apr. 23, 1991. While these ultrathin and flexible absorbent articles work quite well, there remains a need to improve the end soiling performance of these products and to further improve their fit characteristics.

U.S. application Ser. No. 08/665,959 entitled "Generally Thin, Flexible Sanitary Napkin With Stiffened Center", filed on Jun. 18, 1996 by Osborn describes a sanitary napkin that has a stiffened central absorbent core region. Additionally, the napkin comprises flexural-resistance means in its longitudinal side regions. This application also states that this sanitary napkin has a flexure-resistance as measured through the first and second end regions which is less than the flexure-resistance as measured through the central region.

U.S. Pat. No. 5,578,025 issued on Nov. 26, 1996 to May describes a sanitary napkin having stabilizing members joined along it's sides to reduce soiling and improve fit. In one embodiment herein May describes a napkin having stabilizing members extending about the entire periphery of the sanitary napkin, i.e., including end edges. However, May does not disclose or otherwise suggest having stabilizing members or any sort of stiffened and/or absorbent members positioned only at the end regions and/or end edges of the sanitary napkin as in Applicant's embodiment. May's invention is concerned then with providing an entirely stiffened periphery and not just providing stiffness at the end edges.

While the sanitary napkins disclosed in the Osborn patents and application and the May application work quite well, the search for improved sanitary napkins, i.e., sanitary napkins specifically designed to reduce roll-over at their ends, has continued.

As products have become progressively more flexible it has been observed that there is a tendency for the products to roll-over at their end regions and specifically their end edges. This phenomena of end roll-over contributes to both soiling and wearing discomfort.

Thus, it is an object of the present invention to provide the sanitary napkin herein with stabilizing members at its end regions and/or end edges to reduce the tendency of roll over of the product at its ends.

It is also an object of the present invention to provide unitary disposable sanitary napkins herein with improved end region/edge soiling containment performance.

It is an additional object of the present invention to improve the fit of such sanitary napkins during use such that their surface conforms better to the corresponding shape of the human body.

These and other objects of the present invention will be more readily apparent when considered in reference to the following description and when taken in conjunction with the accompanying drawings.

SUMMARY OF THE INVENTION

Accordingly, the present invention provides an absorbent article preferably being a sanitary napkin that comprises a longitudinal centerline, a transverse centerline, a pair of longitudinal edges, two end edges, a first end region extending from one of the end edges toward the transverse centerline, and a second end region extending from the opposite end edge toward the transverse centerline. Also, there is a central region positioned between the first and second end regions. The sanitary napkin further comprises a first surface and a second surface that is faced opposite to the first surface.

The flexure-resistance of the sanitary napkin as measured through the first and second end regions is greater than the flexure-resistance of the sanitary napkin as measured through the central region due to the stabilizing members positioned in the first and second end regions. Preferably, the stabilizing members are positioned immediately adjacent to each end edge. Generally, the sanitary napkin herein comprises first and second end regions that extend from and include the end edges. Each end region comprises about 1/10 to 1/3 of the length of the sanitary napkin starting from an end edge and moving toward the transverse centerline.

In one embodiment of the sanitary napkin herein, the flexure-resistance of the first and second end regions is at least about 25 percent greater than the flexure-resistance of the central region and the longitudinal edges.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in close proximity to the body of the wearer to absorb and contain the various exudates discharged from the body. As used herein, the term "sanitary napkin" or "napkin" refers to an absorbent article that absorbs and contain body exudates, and more specifically, refers to an absorbent article which is worn by females adjacent to the pudendal region, generally external to the urogenital region, and which is intended to absorb and contain menstrual fluids and other vaginal discharges from the wearer's body (e.g., blood, menses, and urine). The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of a unitary disposable absorbent article of the present invention is the catamenial pad, sanitary napkin 20, shown in FIG. 1. Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners or to other absorbent articles such as incontinent pads, and the like. By the terms "flexure-resistance(s)" or "flexural-resistance(s)" it is meant herein the stiffness attributed to an element when that element is acted upon by outside forces, e.g., a stabilizing members flexural-resistance against transverse, compressive forces.

Figure 1:
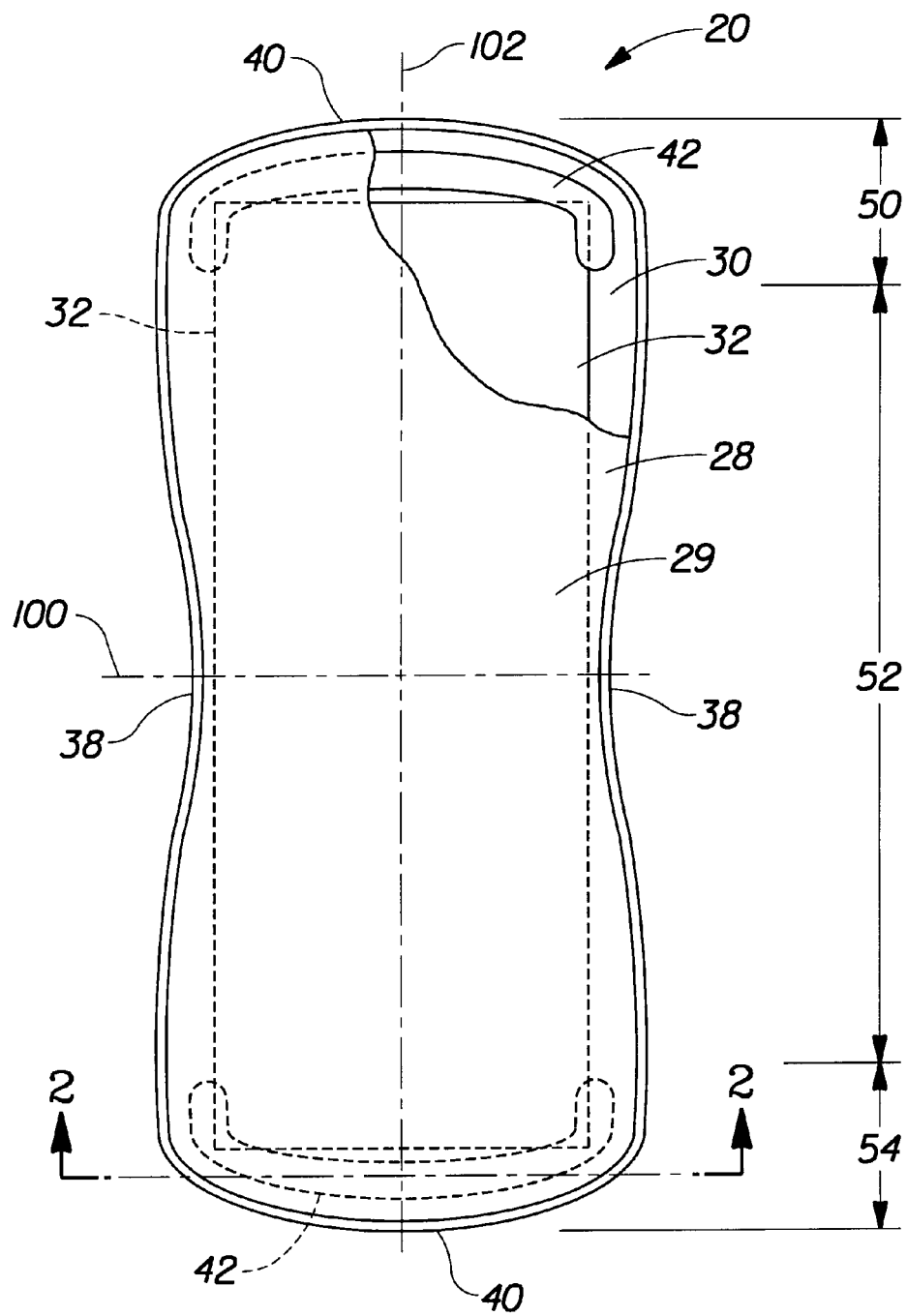
FIG. 1 is a plan view of a preferred embodiment of the present invention having portions cut-away to reveal underlying structure, the outer surface of the sanitary napkin facing the viewer.

FIG. 1 shows a preferred embodiment of the sanitary napkin 20 in which the topsheet 28 and the backsheet 30 have length and width dimensions generally larger than those of the absorbent core 32. The periphery defines the outer perimeter or, in other words, the edges of the sanitary napkin. The periphery comprises the longitudinal edges 38 and the end edges 40. A particularly preferred construction for the sanitary napkin 20 is that described in U.S. Pat. Nos. 4,950,264 and 5,009,653 both entitled "Thin, Flexible Sanitary Napkin", issued to Osborn on Aug. 21, 1990 and Apr. 23, 1991, respectively. Both of these patents are incorporated herein by reference.

FIG. 1 also shows the preferred stabilizing members 42 herein which are principally located adjacent to each end edge 40. As is seen in FIG. 1 both end edges 40 preferably comprise at least one stabilizing member 42. In one embodiment the end edges 40 may actually be formed by at least a portion of the stabilizing members 42. In another embodiment, the stabilizing members 42 arc positioned adjacent to the end edges 40. These stabilizing members 42 provide stiffness at the end edges 40 such that roll over of the edges 40 is reduced. Furthermore, in a preferred embodiment herein, the stabilizing members 42 may partially extend along a portion of the longitudinal edges 38, but stay within the end regions 50 and 54. In some executions it may be preferred that there only be one stabilizing member in one end region 50 or 54 of the sanitary napkin 20.

Each stabilizing member 42 is preferably a separate element joined to the sanitary napkin 20 in one or more end regions 50, 54 (including end edges 40). The term "stabilizing member" refers to a stiffening element joined to the sanitary napkin 20 in one or more end regions 50 and/or 54 to increase the flexural-resistance, i.e., stiffness, of the end regions 50, 54. Note, the stabilizing members herein may either be separate, discrete elements joined to the sanitary napkin and/or elements formed from existing elements within the sanitary napkin, e.g., elements formed from the absorbent core, topsheet, backsheet, acquisition layer, and the like.

Some general ways of providing the sanitary napkin 20 with stiffened end regions 50, 54 or end edges 40 (hereafter end regions/edges) include, but are not limited to: (1) folding any of the components comprising the end regions/edges to create double, or more, thickness of the same; (2) constructing the end regions/edges out of several layers; (3) using stiffer materials; (4) changing the basis weight of components comprising the end regions/edges; (5) placing additional components in the end regions/edges; (6) compression or thermal bonding of the absorbent core to stiffen the end regions or (7) any combinations of the foregoing.

The sanitary napkin 20 has two centerlines, a principal longitudinal centerline 102 and a principal lateral or transverse centerline 100. The term "longitudinal", as used herein, refers to a line, axis or direction in the plane of the sanitary napkin 20 that is generally aligned with a vertical plane which bisects a standing wearer into left and right body halves when the sanitary napkin 20 is worn. This includes a line, axis or direction which is bent, curved or otherwise not strictly parallel to the vertical plane. The term "lateral" refers to the line, axis or direction generally perpendicular to the longitudinal direction and which lies within the plane of the sanitary napkin 20. The sanitary napkin 20 has a longitudinal dimension that runs in the general direction of the principal longitudinal centerline 102 and a lateral dimension that runs in the general direction of the principal lateral centerline 100. The sanitary napkin 20 is typically longer in the longitudinal dimension than in the lateral dimension.

As is shown in FIG. 1, the sanitary napkin 20 is, for the sake of understanding its structure, divided into three sections: a first end region 50, a second end region 54 opposed to the first end region 50, and a central region positioned between the first end region 50 and the second end region 54. For the embodiments herein, stabilizing means 42 are relegated to the first and second end regions 50 and 54. The central region will preferably comprise most or all of the absorbent core 32. The embodiment herein is designed such that the central region 52 will be more pliable, i.e., compressible, to forces applied along the transverse axis. Conversely, the end regions 50, 54 are designed such that they will be more rigid than the central region 52 against applied transverse axial forces. These forces are most notably applied by a wearer's thighs which push against the longitudinal edges 38 of the sanitary napkin 20.

The absorbent core 32 may be any absorbent means which is capable of absorbing or retaining liquids (e.g., menses and/or urine). As shown in FIG. 1 the absorbent core 32 has a body surface, a garment surface, side edges, and end edges. The absorbent core 32 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core 32 may also be varied (e.g., the absorbent core 32 may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 32 should, however, be compatible with the design loading and the intended use of the sanitary napkin 20. Further, the size and absorbent capacity of the absorbent core 32 may be varied to accommodate different uses such as incontinence pads, pantiliners, regular sanitary napkins, or overnight sanitary napkins.

Exemplary absorbent structures for use as the absorbent core 32 of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al. Each of these patents are incorporated herein by reference.

The backsheet 30 and the topsheet 28 are positioned adjacent the garment surface and the body surface, respectively, of the absorbent core 32 and are preferably joined thereto and to each other by attachment means (not shown) such as those well known in the art. For example, the backsheet 30 and/or the topsheet 28 may be secured to the absorbent core 32 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 30 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 30 prevents the exudates absorbed and contained in the absorbent core 32 from wetting articles which contact the sanitary napkins described herein such as pants, night clothing and undergarments. The backsheet 30 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet 30 may permit vapors to escape from the absorbent core 32 (i.e., breathable) while still preventing exudates from passing through the backsheet 30.

The topsheet 28 is compliant, soft feeling, and non-irritating to the wearer's skin. Further, the topsheet 28 is liquid pervious permitting liquids (e.g., menses and/or urine) to readily penetrate through its thickness. A suitable topsheet 28 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

There are a number of manufacturing techniques which may be used to manufacture the topsheet 28. For example, the topsheet 28 may be a nonwoven web of fibers. When the topsheet comprises a nonwoven web, the web may be spunbonded, carded, wet-laid, meltblown, hydroentangled, combinations of the above, or the like. A preferred topsheet is carded and thermally bonded by means well known to those skilled in the fabrics art. A preferred topsheet comprises staple length polypropylene fibers having a denier of about 2.2. As used herein, the term "staple length fibers" refers to those fibers having a length of at least about 15.9 mm (0.625 inches). Preferably, the topsheet has a basis weight from about 18 to about 25 grams per square meter. A suitable topsheet is manufactured by Veratec, Inc., a Division of International Paper Company, of Walpole, Mass. under the designation P-8.

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991, now abandoned, by Aziz, et al., which is incorporated herein by reference. Alternatively, the body surface of the topsheet can be made hydrophilic by treating it with a surfactant such as is described in the above referenced U.S. Pat. No. 4,950,254 issued to Osborn and incorporated herein by reference.

For the purposes of the present invention, a sanitary napkin herein will generally have a caliper in its central region 52 of less than or equal to about 7 mm, preferably less than or equal to about 5 mm, more preferably less than or equal to about 4 mm, and most preferably less than or equal to about 3 mm. The above calipers are to be measured with a comparator gauge having a test weight of 80.0 grams. The comparator gauge should have a comparator foot that weighs 10 grams and has a diameter of 2.44 centimeters. The comparator gauge should have a contact surface area of 4.67 square centimeters.

Figure 4:
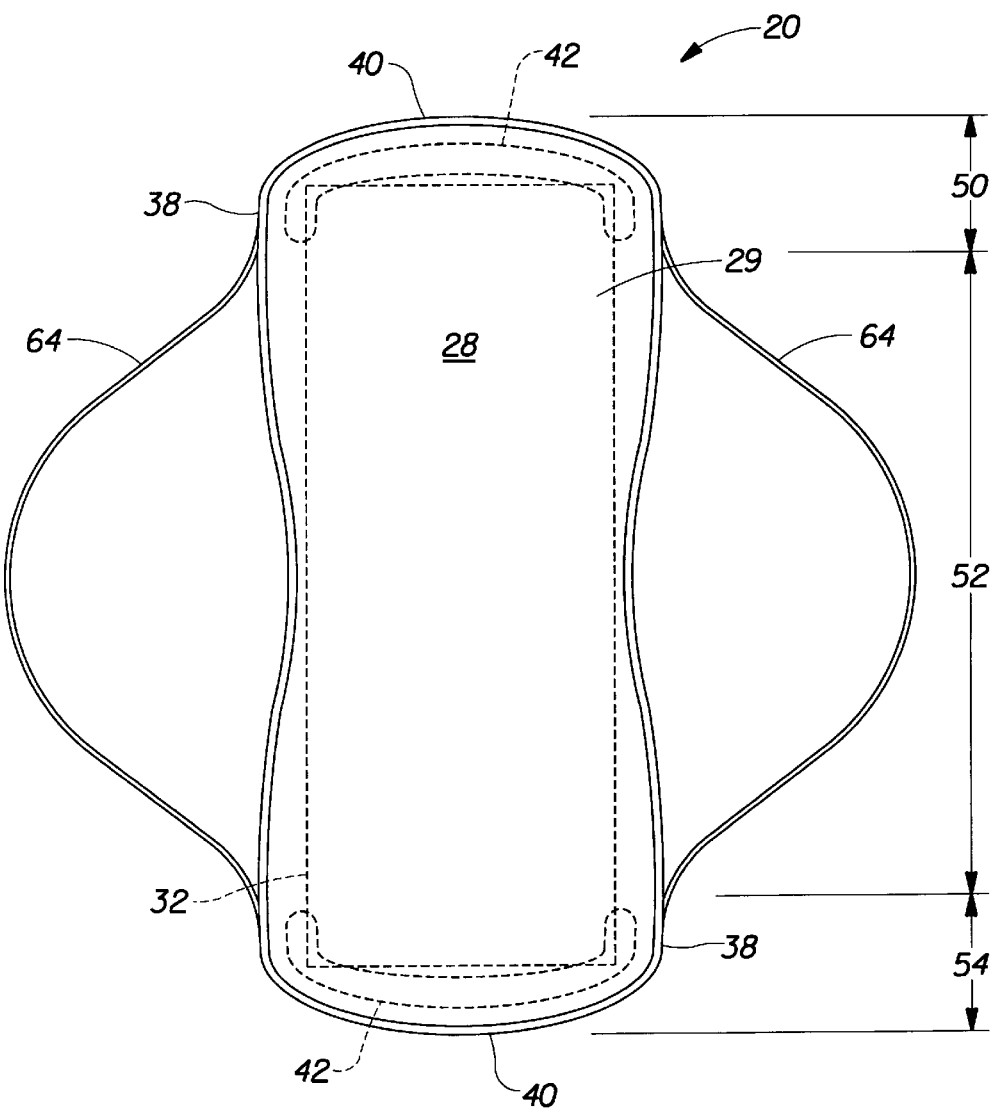
FIG. 4 is a plan view of an alternative embodiment of the present invention.

The sanitary napkins of the present invention can also be provided with any optional additional components that are known in the art. Optional components may include one or several absorbent or fluid transport layers, secondary topsheets, optional interliners, fastening means, and a removable cover strip or release liner. The sanitary napkin may also be provided with flaps or "wings" as shown in FIG. 4 that are folded around the crotch portion of the wearer's undergarment. Examples of such sanitary napkins are more fully described in U.S. Pat. No. 4,589,876 issued to Van Tilburg on May 20, 1986, and in U.S. Pat. No. 4,687,478 issued to Van Tilburg on Aug. 18, 1987, each of which is incorporated herein by reference.

In a preferred embodiment, the garment-facing surface of the backsheet 30 may include means for attaching the sanitary napkin 20 to the undergarment of the wearer, referred to hereinafter as pad attachment means (not shown in FIG. 1). Pad attachment means may include mechanical fasteners or, preferably, adhesive fastening means such as pressure-sensitive adhesive. A removable release liner preferably covers the adhesive fastening means in order to keep the adhesive from drying out or sticking to a surface prior to the usage of the sanitary napkin. The adhesive may be applied to the garment-facing surface of the backsheet in one, two or several parallel strips, or for example two symmetrically opposite convex outwardly oriented strips. The strips of adhesive may be between about 5 to about 35 mm, preferably between 15 mm and 26 mm, in width. Preferably the strips of adhesive are sized and disposed so that the distance between the inside edges of the strips is about 28 mm, and the distance between the outside edges of the strips is about 60 mm. Alternatively, the adhesive may be applied to the backsheet in a generally centered rectangular patch covering about 30% to about 70% of the area of the garment-facing surface of the backsheet. Suitable adhesive may be that specified as "0.6 mil pass" available from Century Adhesive as Product No. 8305-4 or from Anchor Continental, Inc., 3 Sigma Division of Covington, Ohio.

The sanitary napkin 20 of the present invention has divergent flexure-resistance; e.g., the flexure-resistance in the end regions 50 and 54 is held to be generally greater than that in the central region 52. Thus, the sanitary napkin 20 of the present invention is more flexible at its central region 52 and less flexible in its end regions 50 and 54. Preferably, the end regions 50 and 54 of the sanitary napkin 20 of the present invention have flexure-resistances that are at least 25 percent greater and preferably 50 percent greater than at the central region 52. Furthermore, the flexure-resistance at the central region 52 will preferably be less than or equal to about 600 grams while the flexure-resistance at the end regions 50 and 54 will preferably be less than or equal to 1000 grams.

At least one stabilizing member 42 is disposed in each end region 50 and 54, respectively. Each stabilizing member 42 is preferably positioned adjacent to each end edge 40 of the sanitary napkin 20 to increase the flexural-resistance (i.e., the stiffness) of the end regions 50, 54, and end edges 40, beyond that of the central absorbent region 52 so as to allow the sanitary napkin to configure itself into a shape that provides improved fit and allows better absorbent efficiency of the absorbent core 32. Most importantly, the stiffened end regions 50, 54 (including end edges 40) decrease the tendency of a sanitary napkin 20 to flip over or at least reduce partial roll over during wear. Note, when the sanitary napkin 20 herein is in use, thigh compression along longitudinal edges 38 is resisted by the stiffened end regions 50 and 54. Also, during the course of wear by a user, (i.e., during sitting, standing, walking, running, climbing, etc.) it is believed that the napkin 20 will have less tendency to roll-over because of the stabilizing members 42 positioned at the napkin's end regions 50, 54, especially its end edges.

In general, the force required to affect uniform lateral compression throughout the napkin 20 is greater at the first and second end regions 50, 54 (and especially the end edges 40 therein) than at the central region 52. This is by virtue of the stabilizing members 42 located in the end regions 50 and 54. This effect may cause some additional body conformity of the napkin 20 to a user when a user presses her thighs against the napkin side edges 38. By the term "lateral compression" it is meant herein that force required to compress a portion of the sanitary napkin 20 along the transverse axis 100. By the term "end regions" it is meant herein those regions that extend from and that may include the end edges 40 that are between about $\frac{1}{10}$ and $\frac{1}{3}$ of the length of the sanitary napkin toward the transverse centerline.

Figure 2:
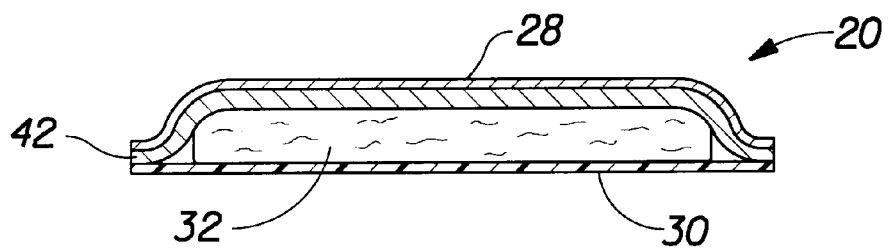
FIG. 2 is a cross-sectional view of the embodiment in FIG. 1.

Stabilizing member 42 may be disposed anywhere through the thickness of the sanitary napkin 20 including on the surface 29 of the topsheet 28, between the absorbent core 32 and the topsheet 28, between the absorbent core 32 and the backsheet 30, or on the garment surface 31 (not shown) of the backsheet 30. As shown in FIGS. 1 and 2, stabilizing members 42 are generally disposed between the topsheet 28 and the backsheet 30. Alternatively, a stabilizing member 42 may also rest on at least a portion of the absorbent core 32 so as to distribute fluid directly back to the core 32. The stabilizing member 42 may be positioned in place between the napkin layers by adhesives, thermal bonding, compression bonding, ultrasonic bonding and the like. Any of the known bonding techniques, e.g., thermal bonding, to combine napkin layers, e.g., joining a core to a topsheet, may be employed herein for the joining of the stabilizing member 42 herein to any one of the sanitary napkin elements. As used herein, the term "joined" includes configurations whereby the stabilizing members are directly affixed to portions of the sanitary napkin and configurations whereby a stabilizing member is indirectly affixed to an intermediate member or members which are in turn affixed to the sanitary napkin. Stabilizing members 42 may also be part of, i.e., attached to, the absorbent core 32.

Stabilizing members 42 may be joined beneath or directly onto the topsheet 28 at a number of different locations, zones, and patterns. For example, a stabilizing member 42 may be joined beneath or onto the topsheet 28 at a point (an attachment point) inward from an end edge 40 so that the stabilizing member 42 may be spaced away from the wearer's surface of the topsheet during use to form a stand-up barrier to the longitudinal flow of body exudates.

FIGS. 3A–3D shows that the stabilizing members 42 may have any of a number of configurations which can provide the necessary stiffness as described herein. The surface area shape, i.e., the shape as viewed from directly overhead, of the stabilizing member can be rectangular, trapezoidal, elliptical or any other shape. In general, the shape of the stabilizing member will depend on performance considerations like comfort and discreteness of the sanitary napkin for the wearer as well as manufacturing capability and packaging compatibility considerations of the producer of the sanitary napkin. According to the present invention, the shape of the stabilizing member can be of any shape such as a rectangular, oval, round, or of a symmetrical or nonsymmetrical type of shape. Particularly preferred shapes are crescent, oval, circular, semi-circular, or rectangular which may be rounded on all or some edges.

Figure 2A:
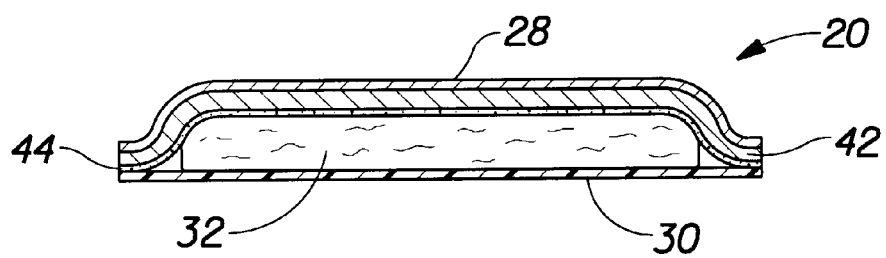
FIG. 2A is a cross-sectional view of an alternative embodiment of the embodiment in FIG. 2.

The stabilizing attachment means 44 (FIGS. 2A and 2B) may be any attachment means known in the art for attaching various elements together in a sanitary napkin, such as stabilizing members 42 attached to a sanitary napkin 20 in the end regions 50 and 54. For example, stabilizing attachment means 44 may comprise adhesives, heat/pressure seals using heat/pressure sealing techniques known in the art, ultrasonic bonds using ultrasonic bonding techniques known in the art, dynamic mechanical bonds using dynamic mechanical bonding techniques known in the art, or any other materials or methods for absorbent articles herein known in the art. The stabilizing attachment means 44 is preferably an adhesive provided such as an adhesive layer 44 as is shown in FIGS. 2A–2B.

Figure 2B:
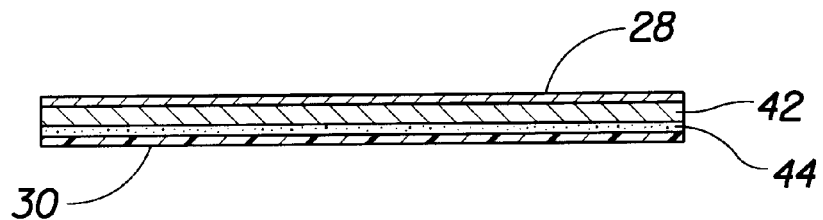
FIG. 2B is a cross-sectional view of an alternative embodiment of the embodiment in FIG. 2.
Figure 3A:
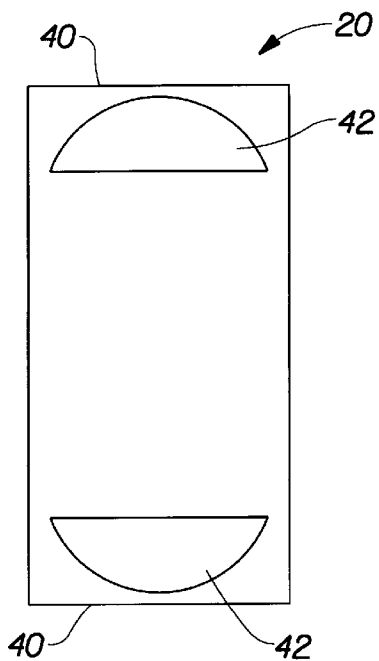
FIG. 3A is a plan view of an embodiment having stabilizing members of an alternative design.
Figure 3B:
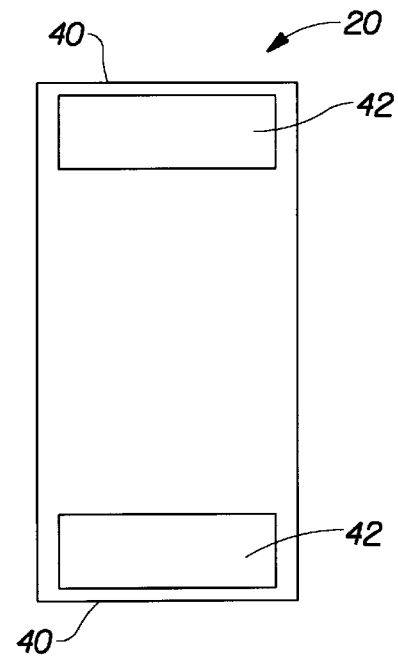
FIG. 3B is a plan view of an embodiment having stabilizing members of an alternative design.
Figure 3C:
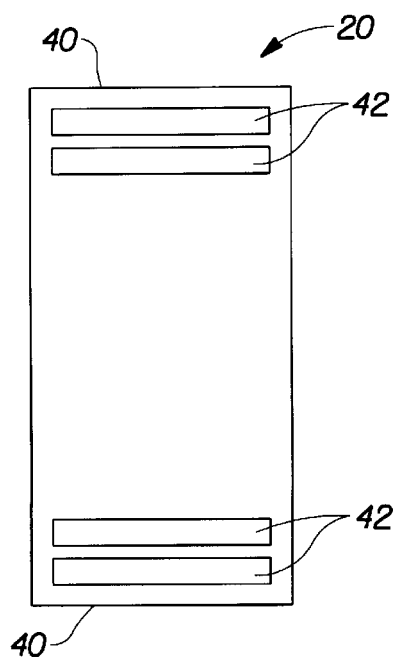
FIG. 3C is a plan view of an embodiment having stabilizing members of an alternative design.
Figure 3D:
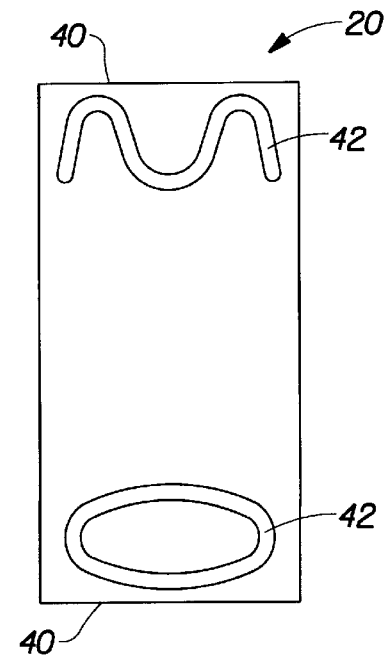
FIG. 3D is a plan view of an embodiment having stabilizing members of an alternative design.

As is seen in FIG. 2B, the stabilizing member 42 is bonded to the backsheet 30 directly by an attachment means 44. In this case, the stabilizing means 42 is not and therefore need not be attached to the absorbent core 32. Also, the stabilizing member 42 may be separately attached to the topsheet 28 by an attachment means 44 or attached to both the topsheet 28 and the backsheet 30 by separate attachment means 44. In FIG. 2A, the stabilizing member 42 may be additionally or separately attached to the topsheet 28 via an attachment means 44. This additional attachment would occur where the stabilizing member 42 is also attached to the absorbent core 32 by an attachment means 44.

The stabilizing member material can be a homogeneous single material, a homogeneous mixture of different materials, or a non-homogeneous combination of different materials (e.g., a layered construction). The stabilizing member materials can be, for example, made from the same materials as the absorbent core materials, the topsheet materials, or the backsheet materials as discussed above.

The stabilizing member material may be a lofted, that is soft and thick, preferably resilient material, such as the airthrough bonded hydrophobic nonwoven with a basis weight of 60 grams as supplied by The Veratec Company of Walpole, Mass.

The stabilizing member material may also, for example, be selected to have an absorbent capacity or may be without absorbent capacity. If the stabilizing member has an absorbent capacity, the material chosen for the stabilizing member preferably maintains a rigidity when wet that reduces foldover at the end regions 50, 54 when these regions are impacted by fluid. Suitable materials include high-loft polyesters, rayons, orlons, other polyolefin materials and blends thereof. In a preferred execution, the stabilizing member is constructed from an absorbent which maintains greater rigidity than the non-reinforced areas. The stabilizing member is preferably wrapped in a web of nonwoven or formed film material as described herein for the topsheet materials.

In one embodiment, a sanitary napkin can have a stabilizing member in the form of an additional absorbent material placed in the end region/edges. The additional absorbent material could comprise any of the materials specified herein as being suitable for use in the absorbent core. From use of these materials, the end regions/edges can be used not only to provide a stabilizing function to the end regions/edges but also provide some absorption of fluid dispersed in a longitudinal direction towards the regions/edges. The additional absorbent material could also comprise capillary channel fibers (described in greater detail below), or cross-linked cellulose fibers. Suitable cross-linked cellulose fibers are described in U.S. Pat. No. 4,888,093, issued Dec. 19, 1989 to Cook et al.; U.S. Pat. No. 4,822,543, issued Apr. 18, 1989 to Dean, et al.; U.S. Pat. No. 4,889,559, issued Dec. 26, 1989 to Schoggen, et al.,; U.S. Pat. No. 4,898,642, issued Feb. 6, 1990 to Moore, et al.; and U.S. Pat. No. 4,935,022 issued Jun. 19, 1990 to Lash et al.

The additional absorbent material could be in any suitable form, including, but not limited to masses or wads of material, single unfolded sheets, folded sheets, strips of material, loose or bonded fibers, multiple layers or laminates of material, layers of foam including polyester and foams developed from high internal phase emulsions (HIPE's) or other combinations of such material. The additional absorbent material could be positioned between any of the components between the topsheet and the backsheet.

Material for a stabilizing member (i.e., hereafter known as "stabilizing material") could, for instance, comprise polymeric gelling agents added or patterned within the end regions and/or along the end edges. In other alternatives, the stabilizing material could include, but not be limited to combinations of polymeric gelling agents and synthetic fibers, natural fibers, or chemically modified natural fibers, such as cross-linked cellulose fibers. In still other alternatives, suitable absorbent fibers such as chemically modified natural fibers may be used as the stabilizing material without the addition of polymeric gelling agents.

One preferred type of stabilizing material is a bi-component fibrous material comprising bi-component fibers having a core of polyethylene which is coated with a sheath of polypropylene. The outside of the bi-component fibers have a lower melting temperature than the inside. Such a material is preferred because the fibers can be heat bonded to each other by melting the outside of the fibers while the inside of the fibers maintain their fibrous integrity instead of melting into an amorphous mass.

Suitable bi-component fibers are commercially available from a company by the name of Chisso. Another material which is suitable for use as the stabilizing material is a fibrous material known as PULPEX, formerly available from Hercules, Inc. of Wilmington, Del.

As previously mentioned herein, another preferred type of stabilizing element for the present invention are those foams developed from high internal phase emulsions (HIPE's) known in the art as functional absorbent materials or FAM foams. Functional absorbent materials are discussed extensively in U.S. Pat. No. 5,387,207, issued to Dyer, et al. and U.S. Pat. No. 5,563,179, issued to DesMarais, et al., each of which are incorporated herein by reference.

The sanitary napkin can be provided with an optional interliner. The optional interliner is used when the sanitary napkin is provided with an absorbent core that has the ability to separate or "decouple" from the backsheet for improved body contact. The concept of decoupling and the characteristics of the interliner are described in U.S. Pat. No. 5,007,906 issued to Osborn, et al. on Apr. 16, 1991 which is incorporated herein by reference.

For each of the embodiments herein stabilizing members 42 may be from any one of the following groups: non-absorbent and pervious; non-absorbent and impervious; non-absorbent and an inherently impervious material but apertured, slit, or the like to make the member itself pervious; or absorbent. Non-absorbent stabilizing members 42 herein may comprise any suitable non-absorbent material. For instance, a non-absorbent stabilizing member 42 may comprise a foam insert, e.g., a functional absorbent material as described in U.S. Pat. No. 5,387,207, issued to Dyer, et al. and is hereby incorporated by reference, or a stiff strip of stiff plastic film.

In a preferred embodiment of the present invention, FIG. 4 shows the sanitary napkin having two flaps 64 each of which are adjacent to and extend laterally from the side edges of the absorbent core. The flaps 64 are configured to drape over the edges of the wearer's panties in the crotch region so that the flaps 64 are disposed between the edges of the wearer's panties and the thighs. The flaps 64 serve at least two purposes. First, the flaps help serve to prevent soiling of the wearer's body and panties by menstrual fluid, preferably by forming a double wall barrier along the edges of the panty. Second, the flaps 64 are preferably provided with attachment means on their garment surface so that the flaps 64 can fold back under the panty and attach to the garment facing side of the panty or one flap 64 to another. In this way, the flaps 64 serve to keep the sanitary napkin 20 properly positioned in the panty. The flaps 64 can be constructed of various materials including materials similar to the topsheet 28, backsheet 30, tissue, or combination of these materials. Further, the flaps 64 may be a separate element attached to the main body of the napkin 20 or can comprise extensions of the topsheet 28 and backsheet 30 (i.e., a unitary construction). A number of sanitary napkins having flaps suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; U.S. Pat. No. 4,589,876 entitled "Sanitary Napkin", which issued to Van Tilburg on May 20, 1986; and U.S. Pat. No. 4,608,047, entitled "Sanitary Napkin Attachment Means", which issued to Mattingly on Aug. 26, 1986. Each of these patents are incorporated herein by reference.

While a preferred sanitary napkin embodiment of the present invention has been described, numerous other sanitary napkin embodiments are disclosed in the literature. These could also be provided with the stabilized end regions/edges of the present invention. Several such sanitary napkins are disclosed in U.S. Pat. No. 4,950,264 issued to Osborn on Aug. 21, 1990, U.S. Pat. No. 5,007,906 entitled "Decoupled Sanitary Napkin" issued to Osborn, et al. on Apr. 16, 1991, U.S. Pat. No. 5,009,653 issued to Osborn on Apr. 23, 1991, U.S. Pat. No. 4,917,697 issued to Osborn, et al. on Apr. 17, 1990, and the aforementioned European Patent Application Publication Nos. 0 335 252 and 0 335 253 published in the name of Buell on Oct. 4, 1989 and European Patent Application Publication No. 0 471 114 A2 on Feb. 19, 1992, and in U.S. patent application Ser. No. 07/605,583 entitled, "Sanitary Napkin Having Components Capable of Separation in Use" filed in the name of Visscher, et al. on Oct. 29, 1990, U.S. patent application Ser. No. 07/630,451 entitled "Sanitary Napkin Having Transversely Segmented Core" filed in the name of Osborn, et al. on Dec. 19, 1990, U.S. patent application Ser. No. 07/707,233 entitled "Sanitary Napkin Having Laterally Extensible Means for Attachment to the Undergarment of the Wearer", filed May 21, 1991 in the name of Osborn, et al.

The sanitary napkin of the present invention can, for example, be provided with a flexure resistant deformation element similar to those described in European Patent Application Publication Nos. 0 335 252 and 0 335 253. The flexure resistant deformation element could be used to assist the sanitary napkin in assuming certain configurations when it is worn. For instance, such an element could be used to make regions of the sanitary napkin predisposed to bend upward or downward when the napkin is worn.

In an alternative embodiment of the sanitary napkin 20 of the present invention the absorbent core 32 of the sanitary napkin 20 may comprise a three layer structure comprising: an acquisition layer; a tissue layer; and a storage layer. The acquisition layer is positioned adjacent the topsheet 28 to rapidly acquire and distribute menses or other body fluids. (Examples of suitable acquisition layers are described in U.S. Pat. No. 5,137,537 issued to Heran & Cooper on Aug. 11, 1992; U.S. Pat. No. 5,009,653 issued to Osborn on Apr. 23, 1991; or WO 93/11725, The Procter & Gamble Company, published on Jun. 24, 1993; each of which is hereby incorporated herein by reference. The tissue layer is positioned between the acquisition layer and the storage layer in order to better distribute menses to the storage layer from the acquisition layer. (The tissue layer is preferably a layer of cellulose tissue such as is marketed by The Procter & Gamble Company under the trademark PUFFS or any other tissue as is known in the art.) The storage layer is designed to retain menses and other body fluids. Thus, the storage layer is positioned adjacent the backsheet 30, between the backsheet 30 and the tissue layer. (The storage layer can be any of the absorbent layers as described herein with respect to an absorbent core but is preferably the superabsorbent laminate such as is described in the above-referenced U.S. Pat. Nos. 4,950,264 and 5,009,653 each issued to Osborn).

Stabilizing members 42 need not be flat, but may have a three-dimensional structure such that it causes better fit within the perineum or gluteal groove allowing discharged exudates to be better retained within the napkin 20. Liquid exudates that are deposited on the core 32 will tend to be distributed radially outward from the place where they are deposited.

The flexure-resistance of the end and central regions of the sanitary napkin herein is measured by peak bending stiffness. Peak bending stiffness is determined by a test which is modeled after the ASTM D 4032.82 CIRCULAR BEND PROCEDURE, the procedure being considerably modified and performed as follows. The CIRCULAR BEND PROCEDURE is a simultaneous multi-directional deformation of a material in which one face of a specimen becomes concave and the other face becomes convex. The CIRCULAR BEND PROCEDURE gives a force value related to flexure-resistance, simultaneously averaging stiffness in all directions. The CIRCULAR BEND PROCEDURE for the embodiments herein have been altered appropriately to rightly measure flexure-resistance in the end regions/end edges of the sanitary napkin 20 herein. However, the complete procedure is disclosed in U.S. Pat. No. 5,009,653 which patent is hereby incorporated by reference herein.

Apparatus

The apparatus necessary for the CIRCULAR BEND PROCEDURE is a modified Circular Bend Stiffness Tester, having the following parts: A smooth-polished steel plate platform which is 102.0×102.0×6.35 millimeters having an 18.75 millimeter diameter orifice. The lap edge of the orifice should be at a 45 degree angle to a depth of 4.75 millimeters. A plunger having an overall length of 72.2 millimeters, a diameter of 6.25 millimeters, a ball nose having a radius of 2.97 millimeters and a needle-point extending 0.88 millimeter therefrom having a 0.33 millimeter base diameter and a point having a radius of less than 0.5 millimeter, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), then the needle-point should not be used. The bottom of the plunger should be set well above the top of the orifice plate. From this position, the downward stroke of the ball nose is to be at the exact bottom of the plate orifice. A force-measurement gauge and more specifically an Instron inverted compression load cell should be used. The load cell has a load range of from about 0.0 to about 2000.0 grams. An actuator to activate the load cell should be used, and more specifically the Instron Model No. 1122 having an inverted compression load cell. The Instron 1122 is made by the Instron Engineering Corporation, Canton, Mass.

Number and Preparation of Specimens

In order to perform the procedure for this test, as explained below, five representative sanitary napkins are necessary. From one of the five napkins having any panty adhesive release paper removed and adhesive blocked, to be tested, some numbers "X" and "Y", each of 37.5×37.5 millimeter test specimens are cut. The "X" specimen is taken from the end regions and will specifically include at least a portion of a stabilizing member 42. The "Y" specimen is taken from the central region 52 and does not comprise any portion of a stabilizing member 42, but rather some portions of all other napkin components within the central region 52. Specimens having portions in which a topsheet is joined directly to a barrier sheet should not be tested. The reason that these specimens are not tested is due to the realization that prior art napkins exist in which a topsheet is joined to a barrier sheet beyond the edges of an absorbent core in the periphery of the napkin, such portions of which are highly flexible. Therefore, a number of different specimens should be tested from each sanitary napkin. The test specimens should not be folded or bent by the test person, and the handling of specimens must be kept to a minimum and to the edges to avoid affecting flexural-resistance properties. From the four remaining sanitary napkins, an equal number of "X" and "Y" of 37.5×37.5 millimeter specimens, identical to the specimens cut from the first napkin, are cut. Thus, the test person should have "X" and "Y" number of sets of five identical specimens.

The procedure for the CIRCULAR BEND PROCEDURE is as follows. The specimens are conditioned by leaving them in a room which is 21.+−.1° C. and 50.+−.2% relative humidity for a period of two hours. The test plate is leveled. The plunger speed is set at 50.0 centimeters per minute per full stroke length. A specimen is centered on the orifice below the plunger such that the body surface 26 of the specimen is facing the plunger and the garment surface 17 of the specimen is facing the platform. Of course, any panty adhesive release paper (if present) is removed, to simulate in-use conditions. Any panty adhesive (if present) should be blocked, using means well known to those skilled in the art, such as glycerin and/or powder, to prevent the specimen from adhering to the platform and an artificially high peak bending stiffness being obtained. If desired, the specimen may be centered over the orifice with the body surface 26 facing the platform and the garment surface 12 facing the plunger to obviate the need for blocking any adhesive which may be present. The indicator zero is checked and adjusted, if necessary. The plunger is actuated. Touching the specimen during the testing should be avoided. The maximum force reading to the nearest gram is recorded. The above steps are repeated until all five of the identical specimens have been tested.

Calculations

The peak bending stiffness for each specimen is the maximum force reading for that specimen. Remember that "X" and "Y" number of sets of five identical specimens were cut. Each set of five identical specimens is tested and the five values received for that set are averaged. Thus, the test person now has an average value for each of the "X" and "Y" sets tested.

The sanitary napkin 20 of the present invention has a liquid capacity great enough to absorb medium to high menstrual flows. Two capacities, which, depending on the size of the sanitary napkin may be the same, are determinable: test capacity and total capacity. Preferably, the sanitary napkin 20 of the present invention has a test capacity of at least about 8.0 grams, more preferably of at least about 15.0 grams, and most preferably of at least about 18.0 grams. Preferably, the sanitary napkin 20 of the present invention has a total capacity of at least about 20.0 grams, more preferably of at least about 30.0 grams, and most preferably of at least about 40.0 grams.

Capacity Testing

The test and total capacities of a sanitary napkin are determined as follows. Any panty adhesive release paper is removed from the napkin to be tested. To determine test capacity, a sample is obtained from a 4.75×14.0 centimeters portion, or any other configuration having 66.5 square centimeters, of the sanitary napkin. The sample is cut from the portion of the sanitary napkin which would be centered under the vaginal orifice when the sanitary napkin is worn. Total capacity is determined using a sample comprising the entire napkin minus any release paper.

The sample is weighed to the nearest 0.1 gram. The sample is then submerged in a beaker of sterile saline (obtainable from the Baxter Travenol Company of Deerfield, Ill.), such that the sample is totally submerged and is not bent or otherwise twisted or folded. The sample is submerged for 10 minutes. The sample is removed from the saline and suspended for two minutes in a vertical position to allow the saline to drain out of the sample. The sample is then placed body facing surface down onto an absorbent blotter, such as the filter paper #631 available from the Filtration Science Corp., Eaton-Dikeman Division of Mount Holly Springs, Pa. A uniform 17.6 grams per square centimeter load is placed over the sample to squeeze excess fluid out. The absorbent blotter is replaced every 30 seconds until the amount of fluid transferred to the absorbent blotter is less than 0.5 grams in a 30 second period. Next, the sample is weighed to the nearest 0.1 gram and the dry weight of the sample is subtracted. The difference in grams is the test or total capacity of the sample, whichever the case may be.

The sanitary napkin 20 should preferably be scaled to the width of the crotch of the underwear of the wearer. A sanitary napkin 20 having a central absorbent width which registers the absorbent with the edges of the underwear crotch is particularly preferred. For relatively narrower underwear crotches, having a width of about 3.7 to about 6.4 centimeters, a sanitary napkin having a central absorbent width 63 of about 3.7 to about 6.4 centimeters works well.

The term "central absorbent width" and a method of measuring the same are described in U.S. Pat. No. 5,009,653.

The sanitary napkins 20 of the present invention are relatively thin. It is preferred to keep the sanitary napkins 20 of the present invention relatively thin so that the sanitary napkins 20 of the present invention will be unobtrusive and the user will have a low awareness of the sanitary napkin while it is being worn. The sanitary napkin 20 shown in FIG. 1 may have a caliper of about 1.9 millimeters. The caliper of a sanitary napkin 20, or various regions thereof, is determined by the following test.

A comparator gauge, and specifically the Ames, Model 130 with dial indicator Model 482, available from the B.C. Ames, Company of Waltham, Mass. is needed. The comparator gauge should have a circular comparator foot made of aluminum and having a weight of 10.0 grams and a contact surface of 5.16 square centimeters. The comparator gauge is zeroed. An 80.0 grams stainless steel weight is placed on the spindle extending above the comparator dial. The comparator foot is raised and the napkin, with any panty adhesive release paper being removed and the adhesive is sprinkled with corn starch, and napkin is placed garment surface down on the base plate. The napkin is positioned on the base plate so that when the foot is lowered it is in the region of the napkin for which the measurement is desired. Try to smooth out or avoid any wrinkles in the napkin. Gently lower the foot onto the napkin. Determine the napkin caliper by reading the comparator dial 30 seconds after the foot comes in contact with the napkin.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sanitary napkin comprising a longitudinal centerline, a transverse centerline, a pair of longitudinal edges, two end edges, a first end region extending from one of said end edges toward said transverse centerline, and a second end region extending from said other end edge toward said transverse centerline, each said first end region and said second end region comprising at least one stabilizing member, and a central region having absorbable material therein, said stabilizing members beings positioned substantially only within said end regions and said central region being positioned between said first and said second end regions, said sanitary napkin comprising:

a first surface; and a second surface opposed to said first surface wherein said central region has a transverse width greater than or equal to about 5 centimeters, and the flexural-resistance of said sanitary napkin as measured through at least one end region is greater than the flexural-resistance of said sanitary napkin as measured through said central region, and said sanitary napkin has a caliper less than about 5 millimeters as measured through said first and said second end regions.

2. The sanitary napkin of claim 1 wherein said first and said second end regions each comprise at least one said stabilizing member positioned adjacent said first and said second end edges.

3. The sanitary napkin of claim 1 having a caliper as measured through said first and said second end regions no greater than about 3 millimeters.

4. The sanitary napkin of claim 3 wherein said first and said second end regions extend from said end edges of said sanitary napkin between about $\frac{1}{10}$ and $\frac{1}{3}$ of the length of said sanitary napkin toward said transverse centerline.

5. The sanitary napkin of claim 1 wherein the flexural-resistance of said first and said second end regions is at least about 25 percent greater than the flexural-resistance of said central region.

6. The sanitary napkin of claim 1 wherein said flexural-resistance of said first and said second end regions is at least about 50 percent greater than said flexural-resistance of said central region.

7. The sanitary napkin of claim 1 wherein the flexural-resistance of said central region is no greater than about 600 grams.

8. The sanitary napkin of claim 1 wherein the flexural-resistance of said first and said second end regions is no greater than about 1000 grams.

9. A sanitary napkin having a longitudinal centerline, a transverse centerline, two longitudinal edges, two end edges, a first end region extending from one of said end edges toward said transverse centerline, a second end region extending from said other end edge toward said transverse centerline, each said first end region and said second end region comprising at least one stabilizing member, said stabilizing member being positioned substantially only within said end regions and a central region positioned between said first and said second end regions, said sanitary napkin comprising:

a liquid pervious topsheet;

a liquid impervious backsheet joined to said topsheet; and an absorbent core positioned between said topsheet and said backsheet, said absorbent core having two longitudinal edges and a width defined by said longitudinal edges wherein said central region has a transverse width greater than or equal to about 5 centimeters, and the flexural-resistance of said sanitary napkin as measured through said first and said second end regions is greater than said flexural-resistance of said sanitary napkin as measured through said central region, said sanitary napkin having a caliper as measured through said first and said second end regions of less than about 5 millimeters.

10. The sanitary napkin of claim 9 wherein said first and said second end edges each comprise at least one said stabilizing member.

11. The sanitary napkin of claim 9 having a caliper as measured through said first and said second end regions no greater than about 3 millimeters.

12. The sanitary napkin of claim 11 wherein said first and said second end regions extend from said end edges of said sanitary napkin between about 1/10 and 1/3 of the length of said sanitary napkin toward said transverse centerline.

13. The sanitary napkin of claim 9 wherein said flexural-resistance of said first and said second end regions is at least about 25 percent greater than said flexural-resistance of said central region.

14. The sanitary napkin of claim 9 wherein said flexural-resistance of said first and said second end regions is at least about 50 percent greater than said flexural-resistance of said central region.

15. The sanitary napkin of claim 9 wherein said flexural-resistance of said central region is no greater than about 600 grams.

16. The sanitary napkin of claim 9 wherein said flexural-resistance of said first and said second end regions is no greater than about 1000 grams.

* * * * *